United States Patent [19]
Smith et al.

[11] Patent Number: 5,238,609
[45] Date of Patent: Aug. 24, 1993

[54] AMINE OXIDE-CONTAINING COMPOSITIONS

[75] Inventors: Kim R. Smith; James E. Borland; Terry Crutcher; Joe D. Sauer, all of Baton Rouge, La.

[73] Assignee: Ethyl Corporation, Richmond, Va.

[21] Appl. No.: 750,193

[22] Filed: Aug. 27, 1991

[51] Int. Cl.⁵ ............................................. C11D 1/75
[52] U.S. Cl. ........................... 252/547; 252/174.21; 252/528; 252/550; 252/DIG. 14
[58] Field of Search .................. 252/547, 174.21, 528, 252/550, DIG. 14

[56] References Cited

U.S. PATENT DOCUMENTS 4,904,359  2/1990  Pancheri et al. ..................... 252/548
5,164,120 11/1992  Borland et al. ..................... 252/546
5,164,121 11/1992  Smith et al. ..................... 252/547
5,167,874 12/1992  Borland et al. ..................... 252/547

Primary Examiner—Asok Pal
Assistant Examiner—P. Achutamurthy
Attorney, Agent, or Firm—Patricia J. Hogan

[57] ABSTRACT

Surfactant compositions which provide acceptable foamability at a lower cost than amine oxide/alkyl sulfate mixtures consist of (A) 5–85% by weight of an amine oxide corresponding to the formula RR'R"NO in which R is a primary alkyl group containing 6–24 carbons and R' and R" are independently selected from methyl, ethyl, and 2-hydroxyethyl, (B) 5–85% by weight of an alkyl sulfate surfactant, and (C) 10–50% by weight of a normally liquid polyalkylene glycol.

15 Claims, No Drawings

AMINE OXIDE-CONTAINING COMPOSITIONS

FIELD OF INVENTION

The invention relates to surfactant compositions and more particularly to such compositions which permit the attainment of good foam volume economically.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of alkyl sulfate anionic surfactants in these compositions permits the attainment of desirable characteristics, including good foamability, it would be desirable to improve their performance and/or the cost using them.

Copending application Ser. No. 750,194 (Borland et al.), filed Aug. 27, 1991, teaches that the performance of alkyl sulfate surfactants can be improved by using them together with certain amine oxides. The surfactant mixtures of Borland et al. are more costeffective than alkyl sulfates or amine oxides alone, but it would be beneficial to make the surfactants still less costly to use if the reduction in cost could be achieved without undue sacrifice of their foamability performance.

SUMMARY OF INVENTION

It has now unexpectedly been found that the cost of using a mixture of an amine oxide and an alkyl sulfate as a surfactant can be reduced without undue sacrifice in foamability performance when the surfactant is a mixture of (A) 5-85% by weight of an amine oxide corresponding to the formula RR'R"NO in which R is a primary alkyl group containing 6-24 carbons and R' and R" are independently selected from methyl, ethyl and 2-hydroxyethyl, (B) 5-85% by weight of an alkyl sulfate surfactant, and (C) 10-50% by weight of a normally liquid polyalkylene glycol.

DETAILED DESCRIPTION

Although an amine oxide used in the practice of the invention may be any compound corresponding to the above formula, it is preferably such an amine oxide in which the primary alkyl group has a straight chain in at least most of the molecules, generally at least 70%, most preferably at least 90% of the molecules. The amine oxides which are especially preferred are those in which R contains 8-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eisocyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

The alkyl sulfate utilized in the mixture may be any of the alkyl sulfates conventionally employed as surfactants. Such anionic surfactants are usually alkali metal or ammonium salts of alkyl sulfates in which the alkyl groups contain 10-18 carbons, and sodium lauryl sulfate is generally preferred.

Polyalkylene glycols which may be used in admixture with the amine oxides and alkyl sulfates are those which are normally liquid, i.e., single polyalkylene glycols, such as polyethylene glycols and polypropylene glycols, and mixtures of such glycols having average molecular weights such as to be liquid at ambient temperature.

Since the amine oxides and alkyl sulfates are typically much more expensive than the polyalkylene glycols, it is not surprising that the use of any amount of an polyalkylene glycol in the surfactant mixtures would reduce their cost. What is surprising is that the mixtures containing the polyalkylene glycols retain acceptable foamability—in fact sometimes have a foamability superior to that of any of their individual components—despite having an ingredient with such poor foamability as a polyalkylene glycol.

The ratio of amine oxide to alkyl sulfate in the mixtures does not appear to be critical to the achievement of acceptable performance. However, as already indicated, the concentration of polyalkylene glycol in the mixtures should not be allowed to exceed about 50% by weight when good foamability is desired; and it is generally preferred that the mixtures contain about 10-40%, more preferably about 10-35% by weight of the polyalkylene glycol component.

The invention is advantageous in that it provides novel surfactant compositions which can provide acceptable levels of foam more economically than the individual components of the compositions. This characteristic of the mixtures makes them valuable for use in the cleaning compositions which require foaming for customer approval, e.g., shampoos, shower gels, and light duty detergents.

When employed in such compositions, the surfactant compositions are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following examples are given to illustrate the invention and are not intended as a limitation thereof. Unless otherwise specified, quantities mentioned in the examples are quantities by weight.

EXAMPLE I

Dissolve varying amounts of N-tetradecyldimethylamine oxide, sodium lauryl sulfate, and PEG-300 (a liquid polyethylene glycol having an average molecular weight of 300) in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1-3 twice, and (5) calculating the average of the three measurements. The proportions of amine oxide, sulfate, and PEG-300 used in preparing each of the solutions and the foam heights obtained from them are shown in Table I.

TABLE I

| Amine Oxide (%) | PEG-300 (%) | Sulfate (%) | Foam Height (mL) |
|---|---|---|---|
| 100 | 0 | 0 | 33 |
| 0 | 100 | 0 | 10 |
| 0 | 0 | 100 | 30 |
| 75 | 12 | 13 | 41 |
| 12 | 13 | 75 | 39 |
| 50 | 25 | 25 | 36 |
| 34 | 33 | 33 | 35 |
| 25 | 25 | 50 | 32 |
| 25 | 50 | 25 | 29 |
| 12 | 75 | 13 | 24 |

EXAMPLE II

Use the procedure of Example I to determine the surfactant efficiencies of 12/13/75 mixtures of N-tetradecyldimethylamine oxide, different liquid polyalkylene glycols, and sodium lauryl sulfate—the different polyalkylene glycols being:

(1) a polyethylene glycol having an average molecular weight of 400 (PEG-400), (2) a polyethylene glycol having an average molecular weight of 600 (PEG-600), and (3) a polypropylene glycol having an average molecular weight of 400 (PPG-400).

The average heights of foam provided by the mixtures containing the PEG-400, PEG-600, and PPG-400 are 40 mL, 37 mL, and 37, respectively.

What is claimed is:

1. A surfactant composition consisting of (A) 5–85% by weight of an amine oxide corresponding to the formula RR'R"NO in which R is a primary alkyl group containing 6–24 carbons and R' and R" are independently selected from methyl, ethyl, and 2-hydroxyethyl, (B) 5–85% by weight of an alkyl sulfate surfactant, and (C) 10–50% by weight of a normally liquid polyalkylene glycol.

2. The surfactant composition of claim 1 having a polyalkylene glycol content of about 10–40% by weight.

3. The surfactant composition of claim 2 having a polyalkylene glycol content of about 10–35% by weight.

4. The surfactant composition of claim 1 wherein R is a primary alkyl group containing 10–18 carbons and R' and R" are methyl.

5. The surfactant composition of claim 4 wherein the amine oxide is N-tetradecyldimethylamine oxide.

6. The surfactant composition of claim 1 wherein the alkyl sulfate is a salt of an alkyl sulfate in which the alkyl group contains 10–18 carbons.

7. The surfactant composition of claim 6 wherein the alkyl sulfate is sodium lauryl sulfate.

8. The surfactant composition of claim 1 wherein the normally liquid polyalkylene glycol is a polyethylene glycol.

9. The surfactant composition of claim 1 wherein the normally liquid polyalkylene glycol is a polypropylene glycol.

10. The surfactant composition of claim 1 consisting of (A) 60–90% by weight of a mixture of (1) an N-alkyldimethylamine oxide in which the N-alkyl group contains 10–18 carbons and (2) a salt of an alkyl sulfate in which the alkyl group contains 10–18 carbons and (B) 10–40% of a normally liquid polyalkylene glycol; each of said oxide and sulfate components constituting at least 5% of the total weight of the composition.

11. The surfactant composition of claim 10 wherein the amine oxide is N-tetradecyldimethylamine oxide, the alkyl sulfate is sodium lauryl sulfate, and the normally liquid polyalkylene glycol is a polyethylene glycol.

12. The surfactant composition of claim 10 wherein the amine oxide is N-tetradecyldimethylamine oxide, the alkyl sulfate is sodium lauryl sulfate, and the normally liquid polyalkylene glycol is a polypropylene glycol.

13. The surfactant composition of claim 10 consisting of (A) 65–90% by weight of a mixture of (1) an N-alkyldimethylamine oxide in which the N-alkyl group contains 10–18 carbons and (2) a salt of an alkyl sulfate in which the alkyl group contains 10–18 carbons and (B) 10–35% of a normally liquid polyalkylene glycol; each of said oxide and sulfate components constituting at least 5% of the total weight of the composition.

14. The surfactant composition of claim 13 wherein the amine oxide is N-tetradecyldimethylamine oxide, the alkyl sulfate is sodium lauryl sulfate, and the normally liquid polyalkylene glycol is a polyethylene glycol.

15. The surfactant composition of claim 13 wherein the amine oxide is N-tetradecyldimethy oxide, the alkyl sulfate is sodium lauryl sulfate, and the normally liquid polyalkylene glycol is a polypropylene glycol.

* * * * *